(12) United States Patent
Lidstrom et al.

(10) Patent No.: US 11,220,700 B2
(45) Date of Patent: Jan. 11, 2022

(54) MICROBIAL CONVERSION OF METHANE

(71) Applicants: LanzaTech New Zealand Limited, Skokie, IL (US); UNIVERSITY OF WASHINGTON THROUGH ITS CENTER FOR COMMERCIALIZATION, Seattle, WA (US); ALLIANCE FOR SUSTAINABLE ENERGY, LLC, Golden, CO (US)

(72) Inventors: Mary Elizabeth Lidstrom, Seattle, WA (US); Marina Georgievna Kalyuzhnaya, San Diego, CA (US); Derek Wayne Griffin, Skokie, IL (US); Nicholas Bourdakos, Skokie, IL (US); Philip Thomas Pienkos, Lakewood, CO (US); Lieve Maria Louisa Laurens, Denver, CO (US)

(73) Assignees: LanzaTech New Zealand Limited, Skokie, IL (US); UNIVERSITY OF WASHINGTON THROUGH ITS CENTER FOR COMMERCIALIZATION, Seattle, WA (US); ALLIANCE FOR SUSTAINABLE ENERGY, LLC, Golden, CO (US)

( * ) Notice: Subject to any disclaimer, the term of this patent is extended or adjusted under 35 U.S.C. 154(b) by 457 days.

(21) Appl. No.: 14/519,075

(22) Filed: Oct. 20, 2014

(65) Prior Publication Data

US 2015/0111265 A1    Apr. 23, 2015

Related U.S. Application Data

(60) Provisional application No. 61/892,547, filed on Oct. 18, 2013.

(51) Int. Cl.
*C12P 5/02* (2006.01)
*C12P 7/64* (2006.01)
*C12P 21/00* (2006.01)

(52) U.S. Cl.
CPC ............... *C12P 7/649* (2013.01); *C12P 5/023* (2013.01); *C12P 7/6463* (2013.01); *C12P 21/00* (2013.01); *Y02E 50/10* (2013.01)

(58) Field of Classification Search
CPC ..................................................... C12P 5/023
See application file for complete search history.

(56) References Cited

U.S. PATENT DOCUMENTS 5,173,429 A    12/1992  Gaddy et al.
5,397,473 A *   3/1995  Jewell ........................ C02F 3/02
                                                               210/610

(Continued)

FOREIGN PATENT DOCUMENTS

CA    2876509    12/2014
EP    117309 A1    9/1984

(Continued)

OTHER PUBLICATIONS

Kaluzhnaya "Taxonomic Characterization of New Alkaliphilic and Alkalitolerant Methanotrophs from Soda Lakes of the Southeastern Transbaikal Region and description of Methylomicrobium buryatense sp.nov" Systematic and Applied Microbiology, 2001, vol. 24, Issue 2, 2001, 166-176.*

(Continued)

*Primary Examiner* — Robert J Yamasaki
*Assistant Examiner* — Charles Zoltan Constantine
(74) *Attorney, Agent, or Firm* — Frank S. Molinaro

(57) ABSTRACT

This invention relates to a process for producing lipids and amino acids from a gaseous substrate comprising methane and oxygen. The process uses a culture of a methanotrophic (Continued)

microorganism in a liquid nutrient medium. The methanotrophic microorganism can be a *Methylomicrobium* bacterium and more specifically *Methylomicrobium buryatense* 5GB1. The lipid products can be in the cellular membrane of the methanotroph and can be extracted in a separate extraction zone.

29 Claims, 3 Drawing Sheets

(56) References Cited

U.S. PATENT DOCUMENTS

| | | | |
|---|---|---|---|
| 5,593,886 | A | 1/1997 | Gaddy |
| 5,807,722 | A | 9/1998 | Gaddy |
| 5,821,111 | A | 10/1998 | Grady et al. |
| 6,136,577 | A | 10/2000 | Gaddy |
| 6,340,581 | B1 | 1/2002 | Gaddy |
| 6,368,819 | B1 | 4/2002 | Gaddy et al. |
| 7,799,550 | B2 | 9/2010 | Moen et al. |
| 2003/0138878 | A1 | 7/2003 | Johannessen et al. |
| 2005/0221465 | A1 | 10/2005 | Moen et al. |
| 2006/0057726 | A1 | 3/2006 | Sharpe |
| 2011/0024453 | A1 | 10/2011 | Larsen |
| 2014/0013658 | A1* | 1/2014 | Silverman ............ C10G 3/00 44/308 |

FOREIGN PATENT DOCUMENTS

| | | |
|---|---|---|
| EP | 132079 B1 | 7/2007 |
| EP | 1641475 B1 | 6/2011 |
| WO | WO1998/00558 A1 | 1/1998 |
| WO | WO2000/68407 A1 | 11/2000 |
| WO | WO2002/08438 A2 | 1/2002 |
| WO | 2002/20728 A2 | 3/2002 |
| WO | WO2007/117157 A1 | 10/2007 |
| WO | WO2008/115080 A1 | 9/2008 |
| WO | WO2009/154683 A1 | 12/2009 |
| WO | WO2010/104922 A1 | 9/2010 |
| WO | 2012/122343 A2 | 9/2012 |
| WO | 2014/012055 A1 | 1/2014 |
| WO | 2014/058761 A1 | 4/2014 |

OTHER PUBLICATIONS

Environmental News Service, "Biotech bacteria could convert methane to liquid diesel", posted Jan. 4, 2013 (https://ens-newswire.com/2013/01/04/biotech-bacteria-could-convert-methane-to-liquid-diesel/).

PCT Search Report (PCT/US2014/061424) dated Feb. 4, 2015.

Chi et al., Oleaginous yeast *Cryptococcus curvatus* culture with dark fermentation hydrogen production effluent as feedstock for microbial lipid production, International Journal of Hydrogen Energy, vol. 36, 2011, pp. 9542-9550.

Shoda M., et al. "Simulation of Growth of Methane-utilising Bacteria in Batch Culture," J Appln Chem Biotechnol, (1975), 25:305-318.

Trotsenko, Y.A., et al., "Biotechnological Potential of Aerobic Methylotrophic Bacteria: A Review of Current State and Future Prospects," Appl Biochem Microbiol, (2005), 41(5): 433-441.

Kalyuzhnaya, M.G., et al. "Functional metagenomics of methylotrophs," Meth Enzymol, (2011), 495:81-98.

Ojala, A., et al. "Genetic systems for moderately halo(alkali)philic bacteria of the genus *Methyolomicrobium*," Meth Enzymol, (2011), 495:99-118.

Canadian Patent Office, Canadian Patent Application No. 2,927,829, Office Action dated Mar. 1, 2017.

Peltola, Petri et al., Effect of copper on membrane lipids and on methane monooxygenase activity of Methylococcus capsulatus (Bath), Arch Microbiol, 1993, pp. 521-525s, vol. 159.

Prior, Stephen D. et al., The Effect of Copper Ions on Membrane Content and Methane Monooxygenase Activity in methanol-grown Cells of Methylococcus capsulatus (Bath), Journal of General Microbiology, 1985, pp. 155-163, vol. 131.

Best, D.J. et al., Methane-oxydizing Activity and Membrane Morphology in a Methanol-grown Obligate Methanotroph, Methylosinus trichosporium OB3b, Journal of General Microbiology, 1981, pp. 73-84, vol. 125.

Sessions, Alex L., Hydrogen isotope fractionation in lipids of the methane-oxidizing bacterium, Geochimica et Cosmochimica, 2002, pp. 3955-3969, vol. 66.

European Search Report for Patent Application 14854055.2, European Patent Office, dated Aug. 25, 2017.

Office Action for Chinese Patent Application 2014800563762, Chinese National Intellectual Property Administration, dated Oct. 18, 2018.

"Methanotrophic Bacteria," 1996, Microbiological Reviews 60(2): 439-471.

Bruslind, L., "Microbial Nutrition," Biology—LibreTexts, Open Oregon State (Oregon State University), Aug. 14, 2020, 9 pages.

* cited by examiner

MICROBIAL CONVERSION OF METHANE

GOVERNMENT RIGHTS

The United States Government has rights in this invention under Contract No. DE-AC36-08GO28308 between the United States Department of Energy and Alliance for Sustainable Energy, LLC, the Manager and Operator of the National Renewable Energy Laboratory.

This invention was made with Government support under US Department of Energy Assistance Agreement No. DE-AR0000350, CFDA No. 81,135. The Government has certain rights in the invention.

FIELD OF THE INVENTION

This invention relates to a process for production of at least one product from a methane-containing feedstock. The process comprises providing a gaseous substrate comprising $CH_4$ and $O_2$ to a bioreactor comprising a culture of at least one methanotrophic microorganism in a liquid nutrient medium to produce at least one product such as lipids and amino acids.

BACKGROUND OF THE INVENTION

The global energy crisis has caused increased interest in alternative approaches to production of fuels. Biofuels for transportation are attractive replacements for gasoline and are rapidly penetrating fuel markets as low concentration blends. Biomass derived biofuel production has emerged as a major approach in increasing alternative energy production and reducing greenhouse gas emissions. The production of biofuels from biomass enables energy independence and has been shown to enhance both the development of rural areas and sustainable economic development.

Traditional liquid biofuels utilise carbohydrate feed stocks such as starch, cane sugar, corn, rapeseed, soybean, palm and vegetable oils. The first generation feed stocks present a number of significant challenges. The cost of these carbohydrate feed stocks is influenced by their value as human food or animal feed, while the cultivation of starch or sucrose-producing crops for ethanol production is not economically sustainable in all geographies. The sustained use of these feed stocks as a source for biofuels would inevitably place great strain on arable land and water resources. Therefore, it is of interest to develop technologies to convert lower cost and/or more abundant carbon resources into fuels.

Second generation biofuels are those produced from cellulose and algae. Algae were selected to produce lipids due to their rapid growth rates and the ability of algae to consume carbon dioxide and produce oxygen.

It has also been demonstrated that biofuels may be produced through microbial conversion of carbon monoxide-containing synthesis gas (syngas). Acetogenic bacteria, such as those from the genus *Acetobacterium, Moorella, Clostridium, Ruminococcus, Acetobacterium, Eubacterium, Butyribacterium, Oxobacter, Methanosarcina, Methanosarcina*, and *Desulfotomaculum*, may be utilised for the production of acetic acid, acetate and other products such as ethanol by the anaerobic fermentation of carbon monoxide, and/or hydrogen and carbon dioxide. These bacteria convert syngas to products via the Wood-Ljungdahl pathway with acetyl co-A synthase being the key enzyme. For examples, various strains of *Clostridium ljungdahlii* that produce acetate and ethanol from syngas are described in WO 00/68407, EP 117309, U.S. Pat. Nos. 5,173,429, 5,593,886, and 6,368,819, WO 98/00558 and WO 02/08438.

One area that has seen increased activity is the microbial synthesis of lipids which comprise the raw materials required for biofuel production. Numerous studies have demonstrated an ability to accumulate lipids through the use of oleaginous yeasts on different substrates such as industrial glycerol, acetic acid, sewerage sludge, whey permeate, sugar cane molasses and rice straw hydrolysate. Again, these second generation biofuel technologies have encountered problems due to high production costs, and costs associated with the transport and storage of the feedstock.

Methane is the second most prevalent greenhouse gas emitted in the United States from human activities. While the lifetime of methane is much shorter than carbon dioxide, it is more efficient at trapping radiation than carbon dioxide, and thus, the comparative impact of methane on climate change is over 70 times greater than carbon dioxide over a 20 year period. Natural gas and petroleum systems are the largest industrial sources of methane, followed by that produced by agriculture and landfill waste. Current strategies for utilisation of methane/reduction of emissions have focussed on the use of methane in natural gas, and that recovered from various industrial processes, as a viable fuel source.

Various methanotrophic bacteria are known throughout nature which, under aerobic conditions, are capable of combining oxygen and methane to form formaldehyde through the enzymes methane monooxygenase and methanol dehydrogenase. The formaldehyde is then incorporated into organic compounds via the RuMP pathway (type I methanotroph) or the serine pathway (type II methanotroph). Eleven genera ofinethanotrophs have been defined, namely *Methylococcus, Methylomonas, Methylomicrobium, Methylobacter, Methylocaldum, Methylovulum, Methylomarinum, Methylomarinovum, Methylothermus, Methylocystis* and *Methylosinus*.

At present, the commercial application of methanotrophic bacteria is limited. Semrau, J. D. (2011) discusses the use of methanotrophs for bioremediation of polluted sites, e.g., degradation of chlorinated hydrocarbons such as trichloroethylene. WO 09/154,683 describes the use of methanotrophs in fuel cells, wherein methane is oxidised by the microbes within the fuel cell to produce electrons. US Publication No. 2005/0221465 and U.S. Pat. No. 7,799,550 describe the use of hydrolysated, homogenized methanotrophic bacteria biomass as nutrient feedstock for fermentation. EP 1641475 describes the use of lipids from methanotrophic bacteria for cholesterol reduction. US Publication No. 2003/0138878 and EP 1320579B 1 describe the use of methanotrophic bacteria biomass as a source of protein. US Publication No. 2006/0057726 describes a set of genetic tools for the positive selection of chromosomal mutations in C1 metabolizing bacteria via homologous recombination. A review by Kalyuzhnaya et al. (2011) describes biotechnological aspects of methanotrophic bacteria and outlines prospects for utilization of methane-utilizing microbes for ectoine production. A study by Shoda et al. (1975) outlines the optimal partial pressures of oxygen and methane for cultivation of methane-utilizing bacteria in batch culture.

There remains a need in the art to produce valuable products, such as biofuels, from gaseous substrates comprising methane. It is an object of the present invention to provide new processes for production of useful products, such as lipids and amino acids, from gaseous substrates comprising methane, and to provide the public with new methods for reducing environmental methane emissions, or to at least provide the public with a useful choice.

SUMMARY OF THE INVENTION

The present invention provides a response to the need in the art. In a first aspect, there is provided a process for production of at least one product by microbial conversion of a gaseous substrate, comprising:
 (a) Providing a gaseous substrate comprising $CH_4$ and $O_2$ to a bioreactor comprising a culture of at least one methanotrophic microorganism in a liquid nutrient medium; and
 (b) microbially converting under fermentation conditions the gaseous substrate to at least one product in the cell biomass selected from the group consisting of lipids, proteins, amino acids and mixtures thereof and excreted fatty acids.

In particular embodiments of the first aspect, the process produces lipids or amino acids, or mixtures thereof. In particular embodiments, the lipids can include, but are not limited to, fatty acids, glycolipids, sphingolipids, saccharolipids, polyketides, sterol lipids, hopanoids, phospholipids and prenol lipids or mixtures thereof. In particular embodiments, the amino acids can include, but are not limited to proline, 5-oxoproline, alanine, aspartate, glutamine and glutamate, or mixtures thereof.

In particular embodiments, the lipids produced by the process can be converted to at least one chemical, fuel or fuel component. For example, the lipids can be converted to compounds selected from the group consisting of renewable diesel, biodiesel fuel, diesel fuel, diesel fuel components, fatty acid methyl esters (FAME) and fatty acid ethyl esters (FAEE) by means well known in the art.

In a second aspect, there is provided a process for production of at least one product by microbial conversion of a gaseous substrate, comprising:
 (a) Providing a gaseous substrate comprising $CH_4$ and $O_2$ to a bioreactor containing a liquid nutrient media and a culture of at least one methanotrophic microorganism;
 (b) microbially converting the gaseous substrate to produce at least one product in the cellular biomass of the microorganism; and
 (c) extracting the at least one product from the cellular biomass of the microorganism.

In particular embodiments, liquid nutrient media is continually fed to the bioreactor. In particular embodiments, the liquid nutrient media is saturated with $O_2$ prior to being fed to the bioreactor. In particular embodiments, the liquid nutrient media is pressurised and saturated with $O_2$ prior to being fed to the bioreactor.

In particular embodiments, at least a portion of unconverted gaseous substrate and/or any gas produced by the microorganism exits the bioreactor through a gas outlet. In particular embodiments, at least a portion of the exit gas is recycled back to the bioreactor for further conversion. In particular embodiments, at least a portion of the exit gas is utilised as a fuel.

In particular embodiments, the culture of at least one microorganism is suspended in a liquid nutrient media. In particular embodiments, the liquid nutrient media is maintained within a pH range from about 6 to about 11. In preferred embodiments, the liquid nutrient media is maintained at a pH from about 8 to about 9.5. In particular embodiments, the temperature of the liquid nutrient media is maintained between about 5 to about 60° C. In preferred embodiments, the liquid nutrient media is maintained at a temperature from about 25 to about 35° C.

In particular embodiments, the one or more microorganism is a methanotrophic bacteria selected from the group consisting of *Methylococcus, Methylomonas, Methylomicrobium, Methylobacter, Methylosarcina, Methylocaldum, Methylomarinum, Methylomarinovum, Methylothermus, Methylovulum, Methylocystis* and *Methylosinus*. In particular embodiments, the methanotrophic bacterium is selected from *Methylococcus capsulatus, Methylomonas methanica, Methylomonas* sp., *Methylosinus trichosporium, Methylobacter marinus, Methylobacter luteus, Methylomicrobium alcaliphilum* and *Methylomicrobium buryatense*. In preferred embodiments, the methanotrophic bacterium is *Methylomicrobium buryatense*.

In particular embodiments, the methanotrophic bacterium is a naturally-occurring strain. In alternative embodiments, the methanotrophic bacterium is an engineered strain. In particular embodiments, the methanotrophic bacterium is a selected strain. In particular embodiments, the selected methanotrophic strain is *Methylomicrobium* strain 5GB1.

In particular embodiments, the process comprises a step of extracting the at least one product from the cellular membrane of the at least one microorganism. In particular embodiments, the extraction step comprises a wet extraction procedure. In particular embodiments, the extraction step occurs in a separate reactor to the conversion step. In particular embodiments, a product stream comprising at least one product and/or at least one microorganism is passed from the reactor to an extraction module.

In particular embodiments, the extraction step comprises a cell disruption step using either high-pressure homogenisation, chemical or physical pretreatments, such as (but not limited to) acid or alkaline pretreatment of the biomass and heating to higher than protein denaturing temperatures (between about 50° C. and about 200° C., preferably between about 75° C. and about 90° C.). In particular embodiments, the extraction step further comprises a solvent extraction step. In particular embodiments, the solvent extraction step separates the product stream into a light phase comprising one or more products and solvent and a heavy phase comprising spent biomass.

In particular embodiments, the solvent is a non-polar alkane or short chain alcohol or any combination of these. In preferred embodiments, the solvent is hexane or alternative short chain alkanes (e.g. pentane, heptane) or short chain alcohols, e.g. butanol, isobutanol, tert-butanol, pentanol or any other solvent (or solvent system combinations) that is compatible with the microbial lipid composition. The more polar the nature of the available microbial products, the more polar the solvent system should be chosen.

In particular embodiments, at least one extracted product is further passed to a product processing module. In particular embodiments, the at least one extracted product is upgraded to renewable diesel, biodiesel fuel, diesel fuel, diesel fuel components, medium chain hydrocarbons and sterol and isoprenoid derivatives, fatty acid methyl esters (FAME) and fatty acid ethyl esters (FAEE).

In particular embodiments, at least a portion of the heavy phase comprising spent biomass from the solvent extraction step is passed to an anaerobic digester where at least a portion of the heavy phase is converted to biogas. At least a portion of the biogas produced by the anaerobic digester can be provided to the bioreactor. In alternative embodiments, at least a portion of the biogas produced by the anaerobic digester is provided to a gas turbine for power generation.

Power generated by the gas turbine may be used to power any step of the process of the invention as described herein.

In particular embodiment, the protein portion of the cell biomass could be separated and used for preparation of protein pellets, which could be used as source of protein for animal feed.

In a third aspect, there is provided a process for production of at least one product by microbial conversion of a gaseous substrate, comprising:
(a) Providing a substrate comprising oxygen and at least one component selected from $CH_4$, $CH_3OH$ and mixtures thereof to a bioreactor containing a liquid nutrient media and a culture of at least one methanotrophic microorganism; and
(b) Microbially converting the gaseous substrate to at least one product selected from lipids and amino acids in the cellular biomass of the microorganism; and
(c) Extracting the at least one product from the cellular membrane of the microorganism.

In particular embodiments of the third aspect, the substrate comprises $CH_4$, $CH_3OH$ and $O_2$. In alternative embodiments, the substrate comprises substantially $CH_3OH$ and $O_2$. In particular embodiments, the substrate comprising $CH_4$ is blended with $CH_3OH$ prior to being provided to the bioreactor. In alternative embodiments, $CH_4$ is converted to $CH_3OH$ prior to being provided to the bioreactor.

In a fourth aspect, there is provided a system for capturing carbon, the system comprising:
(i) a reactor containing a liquid nutrient media and a culture of at least methanotrophic microorganism;
(ii) at least one gas inlet configured to direct a gaseous substrate comprising $CH_4$ and $O_2$ to enter the reactor, and
(iii) at least one gas outlet configured to allow gas to exit the reactor, and
(iv) at least one gas outlet configured to allow gas to exit the bioreactor.

In particular embodiments of the fourth aspect, the system is utilised in a process as described in the first, second and third aspects. In particular embodiments, the system is utilised in a process for microbial conversion of a substrate comprising oxygen and at least one of $CH_4$, $CH_3OH$ to at least one product selected from lipids, proteins, amino acids and mixtures thereof.

In particular embodiments, the reactor is configured to substantially promote growth of one or more microorganisms and/or produce one or more products. In alternative embodiments, the system may comprise a first growth reactor and a second product synthesis reactor.

In particular embodiments, the system comprises a means for passing at least a portion of gas exiting the bioreactor back to the at least one gas inlet of the reactor.

In particular embodiments, the system further comprises an extraction zone for extraction of one or more biomass-based products. In particular embodiments, the system comprises a means for passing a stream comprising at least one products and/or at least one microorganism from the reactor to an extraction zone.

In particular embodiments, the extraction zone comprises multiple extraction units. In particular embodiments, the extraction zone comprises a first, second, third and fourth extraction unit. In particular embodiments, the first extraction unit is configured for chemical or physical treatments of the wet biomass, e.g. high-pressure homogenization, heat treatment and/or the presence of acid or alkaline cell membrane degradation. In particular embodiments, the second extraction unit is configured for solvent extraction. In particular embodiments, the third extraction unit is configured for separation of product/solvent and spent biomass by centrifugation. In particular embodiments, the system comprises a means for passing products, solvent and/or biomass between extraction units.

In particular embodiments, the system further comprises a product processing zone. In particular embodiments, the product processing zone comprises a hydrotreating unit. In particular embodiments, the system comprises a means for passing at least a portion of the product stream from the extraction zone to the product processing zone.

In particular embodiments, the system further comprises an anaerobic digestion zone. In particular embodiments, the system comprises a means for passing at least a portion of the spent biomass to the anaerobic digestion zone.

The invention also includes the parts, elements and features referred to or indicated in the specification of the application, individually or collectively, in any or all combinations of two or more of said parts, elements or features, and where specific integers are mentioned herein which have known equivalents in the art to which the invention relates, such known equivalents are deemed to be incorporated herein as if individually set forth.

BRIEF DESCRIPTION OF THE DRAWINGS

The invention will now be described in detail with reference to the accompanying Figures in which.

DETAILED DESCRIPTION OF THE INVENTION

Definitions

Figure 1:
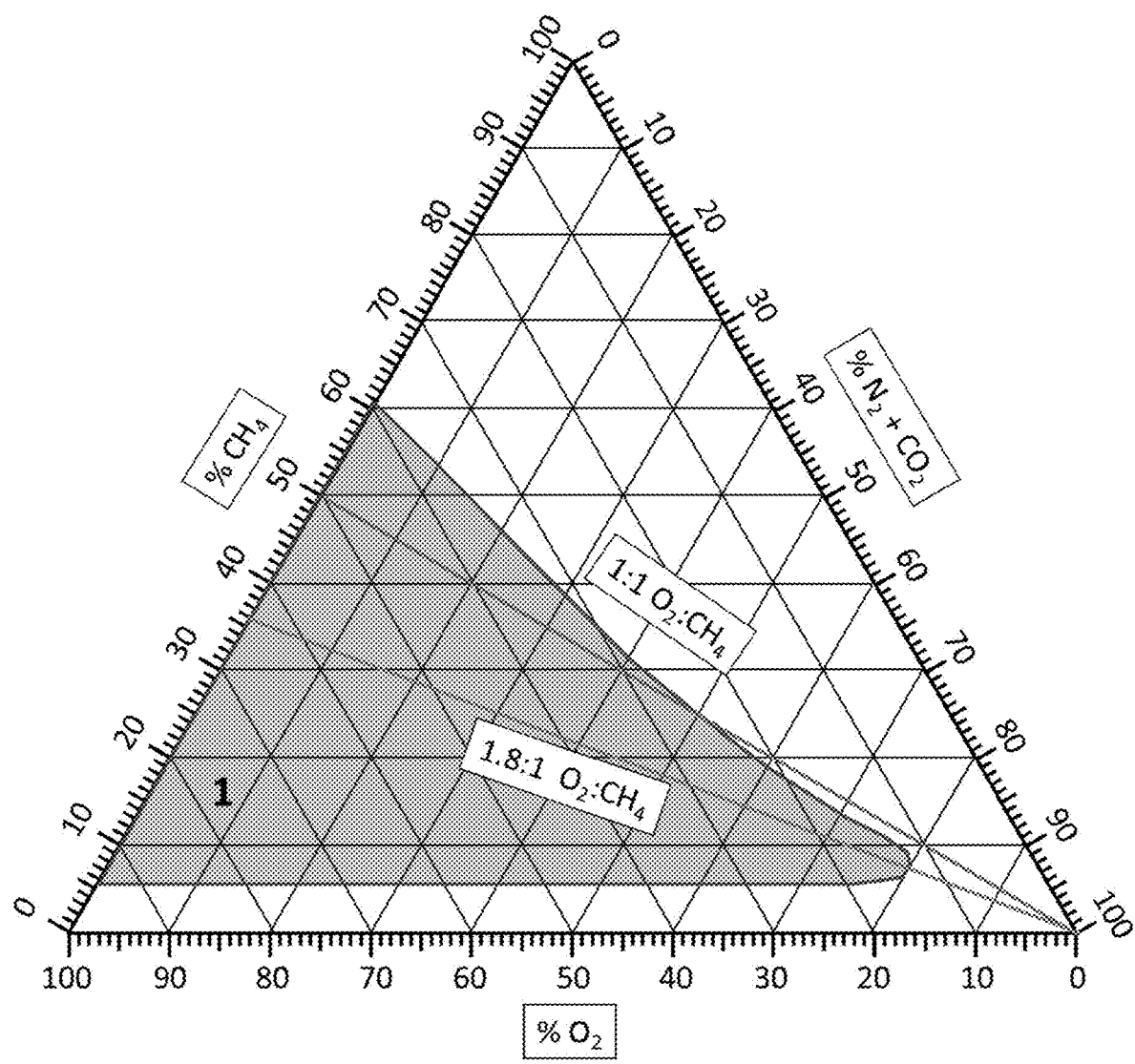
FIG. 1 shows a stoichiometric graph detailing a range of possible stochiometries for microbial $CH_4$ consumption.

Unless otherwise defined, the following terms as used throughout this specification are defined as follows:

The term "reactor" and/or "bioreactor" includes any microbial conversion device consisting of one or more vessels and/or towers or piping arrangements, such as an immobilised cell reactor, a gas-lift reactor, a bubble column reactor (BCR), a circulated loop reactor, a membrane reactor, such as a Hollow Fibre Membrane Bioreactor (HFM BR) or a trickle bed reactor (TBR).

The term "gaseous substrate" includes any gas which contains a compound or element used by a microorganism as a carbon source and optionally energy source in microbial conversion. The gaseous substrate will typically contain a significant proportion of $CH_4$ and $O_2$. Similarly, the term "substrate" includes any gas and/or liquid which contains a compound or element used by a microorganism as a carbon source and optionally energy source in microbial conversion. Examples of liquid substrates include methanol.

The term "biodiesel" refers to a lipid-derived diesel fuel consisting of long-chain alkyl esters. Biodiesel is typically made by chemically reacting lipids with an alcohol to produce fatty acid esters.

The term "renewable diesel" refers to a lipid-derived diesel fuel consisting of long chained alkyl compounds which do not contain oxygen or other hetero atoms such as nitrogen or sulfur. Renewable diesel is typically produced by catalytic hydrogenation, deoxygenation and denitrogenation of lipids optionally followed by catalytic cracking and isomerization of the long chain hydrocarbons to alkanes of chain lengths between 8 and 14 carbons long.

The term "exit gas" includes any gas that exits the reactor through one or more gas outlet. The exit gas will typically contain $CH_4$, $O_2$ and $CO_2$.

The term "liquid nutrient media", "media" and/or "medium" includes a liquid medium comprising nutrients suitable for microbial conversion using one or more microorganisms. The liquid nutrient media will contain vitamins and/or minerals sufficient to permit growth of the microorganism(s) used.

The term "mass transfer" as used herein refers to the transfer of gaseous substrates into the liquid medium where the microorganisms reside.

The term "wet extraction" generally refers to an extraction procedure wherein products are extracted from the microorganism directly without the requirement for dewatering and drying.

Typically wet extraction processes use wet biomass slurries of less than 40% solids (preferably between 10 and 20% solids), where it is still possible for the extraction to occur in a stirred batch reactor in the presence of the solvent, while maximizing the solvent-biomass-mass transfer rates to increase efficiency of product extraction. Wet biomass fractionation is known for algae based on chemical cell disruption (Czartoski et al., WO 2010/104922, "Algae Biomass Fractionation"). Exemplary processes include those described by Czartoski et al. where acid treatment precedes lipid extraction followed by a non-polar solvent extraction process. However, the extraction process is tailored specifically for algae, specifically for non-polar lipids and does not include bacterial or methanotroph biomass or the extraction of polar lipids (derived from substantial bacterial membrane fraction in microbial and bacterial biomass). The existing art on extraction procedures does not include a tailoring of the polarity of extraction solvent to the composition and polarity of the lipids to be extracted, which is the novelty of the extraction systems described in this invention.

The term "light phase" as used herein means a partition of separated matter following an extraction procedure which primarily comprises extracted product and solvent.

The term "heavy phase" as used herein means a partition of separated matter following an extraction procedure which primarily comprises water, spent biomass and any product/solvent carryover.

The term "anaerobic digester" as used herein refers to a reactor which is configured for anaerobic conversion of organic waste to biogas. Typically, the reactor will contain acidogenic bacteria, acetogenic bacteria and/or methanogenic bacteria. The acidogenic bacteria are utilised for conversion of the organic polymers and amino acids into $CO_2$, $H_2$, $NH_3$ and organic acids. The acetogenic bacteria convert the resulting organic polymers into acetic acid, along with additional $CO_2$, $H_2$ and $NH_3$. The methanogenic bacteria convert the resulting acetic acid into $CH_4$ and CO. Reactors suitable for anaerobic digestion may include, but are not limited to, covered anaerobic lagoon digesters, plug flow digesters, complete mixed digesters and dry digesters.

Unless the context requires otherwise, the phrases "microbial conversion" or "microbial reaction" and the like, as used herein, are intended to encompass both the growth phase and product biosynthesis phase of the process.

Methanotrophic single cell protein (SCP) is well-established source of protein for animal feed (Anthony, 1982).

The whole cell protein is typically treated to remove nucleic acids and other phosphorous compounds (like phospholipids). Here we propose to collect cell proteins after lipid extraction, and use those as a source of amino acids for animal feeds.

The term "fermentation conditions" as used herein are those conditions necessary to carry out microbial conversion and includes without limitation temperature of the liquid nutrient medium, composition of the liquid nutrient medium and concentration of individual medium components, pressure of the reactor, mass transfer coefficient of the reactor gas blend used, the ratio of $CH_4$ and $O_2$ in blended gas, the flow rate of the blended gas, the amount of the inoculum, the agitation of bioreactor and pH of the liquid nutrient medium.

The term "wet biomass" as used herein refers to biomass that has been centrifuged to remove at least some of the water present in the biomass. Wet biomass typically contains at least about 30 wt % water.

The term "dry biomass" as used herein refers to biomass that has been first centrifuged, followed by drying, for example by a lyophilizer, to remove about 100% of the water.

Processes for the production of lipids from carbon sources such as glucose, xylose, lactose, glycerol and ethanol are known (Chi et al., "Oleaginous yeast *Cryptococcus curvatus* culture with dark fermentation hydrogen production effluent as feedstock for microbial lipid production" International Journal of Hydrogen Energy, Vol 36, 2011, pp 9542-9550.) Exemplary processes include those described for example by Chi et al. Furthermore, a number of microalgae, such as those of the genus *Chlorella* species, are known to be capable of carrying out the microbial conversion of sugars to lipids. However, methane has not been utilised as a carbon source for microbial production of lipids.

The process of one aspect of the invention involves the microbial conversion, of methane and oxygen in a gas-fed bioreactor to produce lipids, proteins and amino acids. In certain embodiments, the process further involves the extraction of the lipid-based products from the bacterial biomass.

Microorganisms

One necessary part of the process of the invention is at least one methanotrophic bacterium which is capable of microbially converting $CH_4$ and $O_2$ to products such as lipids and amino acids. Any methanotrophic bacteria capable of microbially converting $CH_4$ and $O_2$ to lipids and/or amino acids may be utilised in the accordance with the invention. The methanotrophic bacterium is selected from the group consisting of *Methylococcus, Methylomonas, Methylomicrobium, Methylobacter, Methylocaldum, Methylomarinum, Methylovulum, Methylomarinovum, Methylothermus, Methylocystis, Methylosinus* and mixtures thereof. In particular embodiments, the methanotrophic bacterium is selected from *Methylococcus capsulatus, Methylomonas methanica, Methylomonas* spp., *Methylosinus trichosporium, Methylomarinum vadi, Methylobacter marinus, Methylomarinum vadi, Methylomicrobium alcaliphilum* and *Methylomicrobium buryatense.*

In further embodiments, the methanotrophic bacterium is selected from the genus *Methylomicrobium*. Methanotrophic bacteria of this genus are typical group I methanotrophs, using the ribulose monophosphate (RuMP) Pathway to assimilate carbon.

In preferred embodiments, the methanotrophic bacterium is *Methylomicrobium buryatense*. This species is mesophilic, although able to grow at 10° C.-45° C. In batch culture, growth occurs at a pH between 6-11, preferably pH 8.0-9.5, and with between 0.1-8% NaCl, preferably 0.75% NaCl. This species contains particulate methane monooxygenase (pMMO) and soluble methane monooxygenase (sMMO) (Kaluzhnaya et al., 2001).

The methanotrophic bacterium can be a naturally occurring bacterium or an engineered strain. For example, the methanotrophic bacterium is an engineered *Methylomicrobium* strain that has enhanced growth properties over the parental strain. In particular embodiments, the methanotrophic bacterium is a selected *Methylomicrobium* strain. One exemplary selected strain suitable for use in the present invention is *Methylomicrobium buryatense* 5GB1, which is rifamycine resistant variant of the wild type and has a mutation in rpoS-gene (MBURv2_50058), which has a 309 base pair insertion that results in a stop codon after 218 aa (out of 327aa for wild-type). In certain embodiments of the present disclosure the improved strain has a specific growth rate of approximately 0.24 (culture doubling time of 3 hr) on optimized growth medium (see Example 1.

Feedstock

Whatever the methanotrophic bacterium is used in carrying out the process of the invention, it requires a carbon source and a source of oxygen to produce lipids and/or amino acids. Carbon sources include without limitation methane, methanol and mixtures thereof. Methane can be obtained from a source selected from the group consisting of, but not limited to, natural gas, synthetic natural gas, natural gas hydrates, stranded natural gas, shale gas, flared gas, coal mine methane, coal bed methane, methane produced from catalytic cracking of olefins or organic matter, landfill gas, biogas, associated petroleum gas, agricultural generated methane, and methane produced as an unwanted by product from CO hydrogenation and hydrogenolysis reactions such as the Fischer-Tropsch process. The largest source of $CH_4$ globally is from natural gas and petroleum systems.

The methanol may be derived from the catalytic conversion of carbon monoxide and hydrogen. Alternatively, the $CH_3OH$ is derived from the catalytic conversion of $CH_4$. In particular embodiments, a gas stream comprising $CH_4$ is catalytically converted to $CH_3OH$ prior to being provided to the reactor. In some embodiments, the process of the invention is integrated with a $CH_3OH$ synthesis process. For example, at least a portion of $CH_3OH$ from a $CH_3OH$ synthesis process, such as a methanol production plant, may be diverted to a reactor for utilisation in the process of the invention.

In various embodiments of the invention, methanol and methane can be blended together and fed to the bioreactor Another component necessary for the methanotrophic bacterium to grow and produce lipids and/or amino acids is oxygen or an oxygen source. Typical sources of oxygen include but are not limited to air, enriched air, $O_2$ from fractional distillation, pressure swing adsorption, an oxygen concentrator, electrolysis of water and liquid $O_2$. The ratio of oxygen to carbon source can be varied in order to improve production of the desired products or to optimise the efficiency of the microbial reaction and ultimately improve production or to improve growth. The ratio of $O_2$ to $CH_4$ in the gaseous substrate can range from about 5:1 to about 1:1. In particular embodiments, the gaseous substrate provided to the bioreactor comprises $O_2$ to $CH_4$ at ratio ranging from about 2.5:1 to about 1:1. In particular embodiments, the gaseous substrate provided to the bioreactor comprises $O_2$ to $CH_4$ at a ratio ranging from about 1.5:1 to about 1:1. The reaction stoichiometry between $CH_4$ and $O_2$ will vary depending on the pathway utilised by the microorganism(s).

The range of possible stoichiometries for microbial $CH_4$ consumption is illustrated in FIG. 1.

As illustrated in FIG. 1, the stoichiometry may require operation of the reactor wherein the volumes of $CH_4$ and $O_2$ are provided in the flammable range (1). It is preferable that the reactor is operated wherein non-flammable conditions are present in the reactor, and therefore 96% or greater conversion of $CH_4$ is required when operating at a 1.8:1 $O_2$ to $CH_4$ inlet gas ratio in order to create a non-flammable condition in the reactor.

Figure 2:
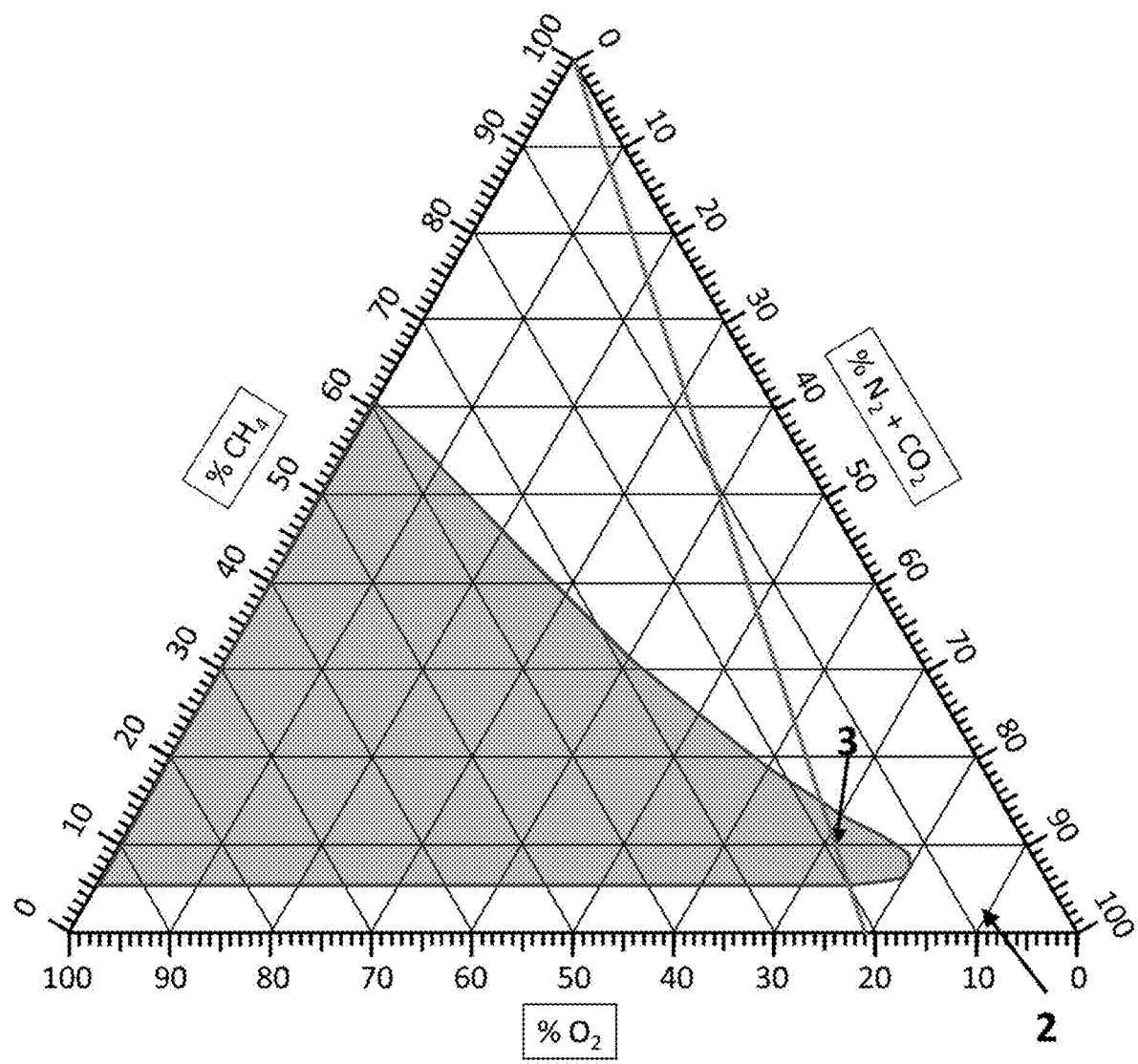
FIG. 2 shows a stoichiometric graph detailing a range of possible stochiometries for microbial $CH_4$ consumption when operating with air.

In particular embodiments, the gaseous substrate utilised in the process comprises air as an alternative to $O_2$. When operating with air in lieu of $O_2$, the operating condition in the reactor can be run outside of the flammable range depending on the $CH_4$ conversion in the reactor. A range of stoichiometry for operation with air is illustrated in FIG. 2, wherein (1) represents the flammable region, (2) represents the range of stoichiometry, (3) represents the inlet gas composition, and (4) represents the air line. In certain embodiments, $CH_4$ conversion above 40% will lead to a non-flammable condition within the reactor utilising a 1.8:1 $O_2$ to $CH_4$ inlet gas ratio. This simplifies the reactor design in terms of ignition source reduction.

When the carbon source is methanol, the concentration of $CH_3OH$ in the growth medium can vary from about 1% (v/v) to about 5% (v/v). In particular embodiments, the ratio can be from 1:1.2 to about 1:1.5. For optimal methanol utilization the strain should be grown at fully aerobic condition. In particular embodiments, a substrate comprising $CH_3OH$ is provided to the reactor in the initial stages of the process in order to optimise microbial growth. Once an optimal growth rate of the one or more microorganisms is established, the substrate may be changed to a substrate comprising $CH_4$ and $O_2$.

The carbon source and oxygen source can be fed to the bioreactor as one stream or as separate streams. For example a natural gas stream can be blended with an oxygen containing stream, e.g. air, to provide the desired $O_2:CH_4$.

In another embodiment a substrate comprising methane and methanol can be fed into the reactor and an oxygen containing stream can be separately fed into the reactor. A methanol liquid stream can be fed separately from the methane gaseous stream.

Blended gas streams may also have further advantages, particularly in instances where a gas stream comprising $CH_4$ or $CH_4$ and $O_2$ is intermittent in nature. For example, an intermittent gas stream comprising $CH_4$ or $CH_4$ and $O_2$ may be blended with a substantially continuous stream comprising $CH_4$ or $CH_4$ and $O_2$ and provided to the reactor. In particular embodiments, the composition and flow rate of the substantially continuous stream may be varied in accordance with the intermittent stream in order to maintain provision of a substrate stream of substantially continuous composition and flow rate to the fermenter.

Regardless of the ratio of oxygen:carbon source being fed to the reactor, it is important that sufficient oxygen is dissolved in the liquid nutrient medium in order to facilitate uptake by the bacterium. Generally the dissolved oxygen should range from about 0.1% to about 100% saturation of air at atmospheric pressure. In some embodiments the dissolved oxygen is in the range of about 0.1 to about 40% saturation of air at atmospheric pressure. It is generally desirable to have the dissolved oxygen be less than about 1 mM/L of $O_2$.

The process of the invention may be integrated with other processes involving the synthesis of products from gaseous substrates. An example of such processes includes the production of alcohols and/or acids through anaerobic fermentation of gaseous substrates comprising CO, $CO_2$ and/or $H_2$. Exemplary processes include those described for example in WO 2007/117157 and WO 2008/115080, as well as U.S. Pat. Nos. 6,340,581, 6,136,577, 5,593,886, 5,807,722 and 5,821,111, each of which is incorporated herein by reference. In such embodiments, gas streams comprising $CH_4$ along with CO, $CO_2$ and/or $H_2$, for example natural gas or landfill gas, may undergo any gas separation process known in the art in order to separate the components or elements of the gas. The separated $CH_4$ may then be utilised in the process of the invention, while the CO, $CO_2$ and/or $H_2$ may be utilised in an anaerobic fermentation process.

Reactor

The culturing of the microorganism(s) and microbial conversion of methane to one or more products may be carried out in any suitable bioreactor, such as an immobilised cell reactor, a gas-lift reactor, a bubble column reactor (BCR), a circulated loop reactor, a membrane reactor, such as a Hollow Fibre Membrane Bioreactor (HFM BR) or a trickle bed reactor (TBR). Also, in some embodiments of the invention, the bioreactor may comprise a first growth reactor in which the micro-organism(s) are cultured, and a second product synthesis reactor, to which broth from the growth reactor may be fed and in which various products (e.g. acids) may be produced.

The bioreactor comprises a liquid nutrient media which contains the desired bacteria and will be fed a gaseous substrate comprising $CH_4$ and $O_2$. In particular embodiments, liquid nutrient media is continually fed to the reactor. In particular embodiments, the liquid nutrient media is saturated with $O_2$ prior to being fed to the reactor. In particular embodiments, the liquid nutrient media is pressurised and saturated with $O_2$ prior to being fed to the reactor.

The liquid nutrient media will contain nutrients suitable for microbial conversion using the desired bacteria and will further contain vitamins and/or minerals sufficient to permit growth of the micro-organism(s) used. Media suitable for the culturing of methane consuming bacteria are known in the art. For example, suitable media are described in Kaluzhnaya et al., 2001 and Ojala et al., 2011. In particular embodiments, the media is a minimal mixture of salts. The composition may vary in salt content. Typical nutrient medium compositions are set forth in Table 1.

TABLE 1

Nutrient Medium Composition for Cultivation of Methanotrophic Cultures

| Compound | Range (g/L) |
| --- | --- |
| $KNO_3$ | 0-1 |
| $MgSO_4$ | 0.04-1 |
| $CaCl_2$ | 0.01-0.2 |
| $Na_2HPO_4$ | 0.2-1 |
| $KH_2PO_4$ | 0.1-1 |
| NaCl | 0-10 |
| $Na_2CO_3$ | 0-1 |
| $NaHCO_3$ | 0-8.4 |
| $Na_2EDTA$ | 0-5 |
| $FeSO_4 \times 7H_2O$ | 0.002-0.2 |
| $ZnSO_4 \times 7H_2O$ | 0.0001-0.8 |
| $MnCl_2 \times 4H_2O$ | 0.00003-0.04 |
| $CoCl_2 \times 6H_2O$ | 0.0002-0.2 |
| $CuSO_4 \times 5H2O$ | 0.0001-0.008 |
| $NiCl_2 \times 6H_2O$ | 0.00002-0.02 |
| $Na_2MoO_4 \times 2H_2O$ | 0.00003-0.05 |
| $H_3BO_3$ | 0-0.06 |

In some embodiments of the present invention, the media used to grow M. buryatense 5GB1 comprises NMS culture media. In further embodiments of the present invention, the media used to grow M. buryatense 5GB1 comprises $MgSO_4*7H_2O$ ranging from about 0.04 g/L to about 1 g/L, $CaCl_2*6H_2O$ ranging from about 0.007 g/L to about 0.2 g/L, NaCl, $KH_2PO_4$, $Na_2CO_3$, $Na_2$-EDTA, $FeSO_4*7H_2O$, $ZnSO_4*7H_2O$, $MnCl_2*4H_2O$, $H_3BO_3$ ranging from about 0.02 g/L to about 0.03 g/L, $CoCl_2*6H_2O$ ranging from about 0.02 g/L to about 0.2 g/L, $CuCl_2*2H_2O$, $NiCl_2*6H_2O$, and $Na_2MoO_4*2H_2O$ ranging from about 0.003 g/L to about 0.05 g/L.

In some embodiments of the present invention, the media used to grow M. buryatense 5GB1 comprises at least one nitrogen source such as $KNO_3$, $NaNO_3$, $NH_4Cl$, $(NH_4)_2SO_4$, urea, or mixtures thereof. In further embodiments of the present invention, the media used to grow M. buryatense 5GB1 comprises at least one nitrogen source comprising $KNO_3$, $NaNO_3$, or mixtures thereof It has been found that some of the nutrients being added affect the growth rate and the amount of lipids produced by the particular bacterium. In particular it is desirable to have a $Cu^{++}$ uptake of at least 7.5 μmol/gDCW. Since the amount of copper may eventually become a poison to the bacterium, it is desirable to have the $Cu^{++}$ concentration be within the range of about 7 μM to about 20 μM. Similarly it is desirable to have the $Fe^{++}$ concentration be within the range of about 5 μM to about 15 μM (Table 2). Similarly the $NO_3^-$ uptake should vary from about 5 mmol/gDCW to about 8 mmol/gDCW. Additionally the $PO_4^{-3}$ should range from about 1.4 mmol/gDCW to about 2 mmol/gDCW.

The bioreactor is configured to provide enough mass transfer to allow the microorganism(s) to access the $CH_4$ (and or $CH_3OH$) and $O_2$. Long gas residence times generate high gas uptake by the microorganism(s). In particular embodiments, the reactor is a circulated loop reactor comprising a riser segment and a downcomer segment through which the gaseous substrate and liquid media are circulated. The reactor may additionally include a wide range of suitable gas/liquid contact modules that can provide effective mass transfer of a gaseous substrate necessary to improve the efficiency of microbial conversion. A contact module provides a unique geometrical environment allowing gas and liquid to mix thoroughly along a set flow path, causing the entrained gas to dissolve in the liquid more uniformly. By way of example, these contact modules include, but are not limited to, a matrix of structured corrugated metal packing, random packing, sieve plates and static mixers, all of which have a range of well-known types and densities and are widely commercially available.

In accordance with particular embodiments, the mass transfer rate of the gaseous substrate to the microbial culture can be controlled such that the microbial culture is supplied with substrate at or towards an optimum supply rate. In the reactors, the mass transfer rate can be controlled by controlling partial pressure of the gas substrate and/or by controlling the liquid flow-rate or gas holdup. In particular embodiments, the mass transfer is controlled by controlling the partial pressure of the gaseous substrate entering the reactor.

In particular embodiments, the pH of the medium is maintained from about 6 to about 11. More particularly the pH varies from about 8.0 to about 9.5. The pH may be controlled by the addition of carbonate or bicarbonate, or by the addition of acids and bases to the medium as required. In particular embodiments, the temperature of the liquid nutrient media is maintained from about 5 to about 65° C., preferably from about 20 to about 40° C. and most preferably from about 25 to about 35° C.

Production of Products

The process of the invention produces lipid-based products from the microbial conversion of $CH_4$ by the methanotrophic microorganisms in the bioreactor. In various embodiments, the lipids are contained in the membrane fraction of the bacterial biomass. The lipid fraction of the overall biomass volume will be determined by the growth conditions in the reactor. In particular embodiments, the lipids contained in the membrane fraction of the bacterial biomass account for about at least 5% of the dry weight of the bacteria. In particular embodiments, the lipids contained in the membrane fraction of the bacterial biomass account for at least about 20% or at least about 40% of the dry weight of the bacteria. One of the waste gases produced as part of the microbial conversion is $CO_2$. The $CO_2$ can leave with any unreacted gases in the gas phase or some of it may be contained in the liquid broth. The amount which leaves in the gas phase versus liquid broth will depend on the pH of the broth with higher pH favoring $CO_2$ in the liquid broth.

Figure 3:
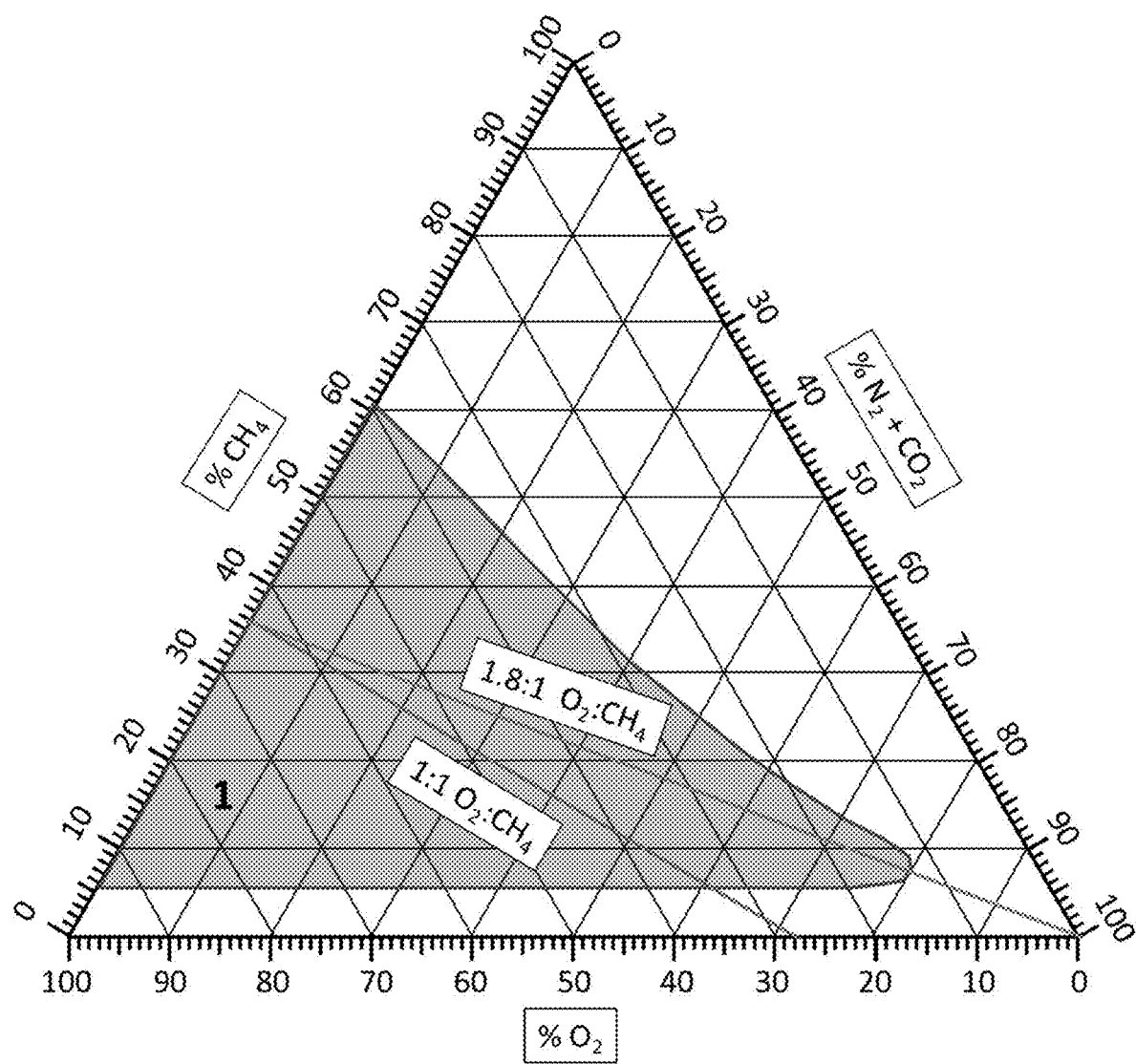
FIG. 3 shows a stoichiometric graph detailing a range of possible stoichiometries for microbial $CH_4$ consumption in favour of lipid production when operating with limited $O_2$.

In particular embodiments, a limited $O_2$ supply to the reactor will favour the production of lipids by the microorganism(s). Adequate $CH_4$ supply with a limited supply of $O_2$ can lead to both a faster growth rate and enhanced lipid formation by the culture. Therefore, in particular embodiments, a gaseous substrate comprising an excess of $CH_4$ is provided to the reactor for lipid product generation by the culture. In particular embodiments, a limited $CH_4$ supply to the reactor will favour the production of lipids by the microorganism(s). Adequate $O_2$ supply with a limited supply of $CH_4$ can lead to both a faster growth rate and enhanced lipid formation by the culture. Therefore, in particular embodiments, a gaseous substrate comprising an excess of $O_2$ is provided to the reactor for lipid product generation by the culture. In particular embodiments favouring lipid production, the uptake by the bacterium of the gaseous substrate is at a ratio ranging from about 1:1 to about 2.5:1 $O_2$ to $CH_4$. In preferred embodiments favouring lipid production, the uptake of $O_2$ and $CH_4$ varies at a ratio ranging from about 1.3:1 to about 1:1. It is desirable that the bacteria growth rate be at least 0.08 $hr^{-1}$, or at least 0.12 $hr^{-1}$, or at least 0.2 $hr^{-1}$, or at least 0.4 $hr^{-1}$. A range of stoichiometry operating with limited $O_2$ and favouring lipid production is illustrated in FIG. 3, wherein (1) represents the flammable region.

In particular embodiments, the process produces lipids including fatty acids, glycolipids, sphingolipids, saccharolipids, polyketides, sterol lipids, hopanoids, phospholipids and prenol lipids with fatty acid (and resulting hydrocarbon) having chain lengths from about 12 to 20 carbon. Specific examples of lipids include but are not limited to lauric acid, myristic acid, palmitic acid, palmitoleic acid, stearic acid, vaccenic acid, phosphatidylcholine, triglycerides, glycerols, and mixtures thereof. Specific fatty acid content is shown in Example 1, Table 3.

In addition to lipid production, the process of the invention can also produce amino acids. In particular embodiments, amino acids produced by the microorganism include, but are not limited to, ectoine, proline, 5-oxoproline, alanine, aspartate, glutamine and glutamate. One example of amino acid production is shown in Table 3 which is presented in Example 3. Production of amino acids by the microorganism may result from cultivation at high salinity (3-8% NaCl).

The reactor should desirably be operated under appropriate conditions for the microbial conversion of gas to desired products to occur. Reaction conditions that should be considered include pressure, temperature, gas flow rate, liquid flow rate, media pH, media redox potential, agitation rate (if using a continuous stirred tank reactor), inoculum level, maximum substrate concentrations to ensure that either the $CH_4$, $CH_3OH$ or $O_2$ in the liquid phase does not become limiting, and maximum product concentrations to avoid product inhibition.

In certain embodiments of the invention it may be beneficial to the process at elevated partial pressures. Higher pressures in the reactor may impact lipid formation and growth of the microorganisms. In particular embodiments, the reactor is maintained at a pressure from about atmospheric to about 3,000 kPag. In other embodiments the pressure can be from about 20 kPag to about 2,000 kPag.

In certain embodiments, the sodium concentration of the medium may have an effect on growth and production rates of methanotrophic microorganisms. In particular embodiments, the sodium concentration of the medium is brought to a desired level using a salt, preferably NaCl. In such instances, the pH of the medium is controlled using acids and bases that do not contain sodium. In preferred embodiments, the sodium concentration is maintained between about 120 and about 210 mM (as the cation).

In various embodiments, the gas composition of the process is determined using gas chromatography by regular t sampling of both the inlet and outlet gas. This allows for the monitoring of $CH_4$, $CO_2$, $O_2$ and inert species such as nitrogen in the gas, as well as hydrogen generated by the bacterial metabolism. In particular embodiments, the $O_2$ level in the reactor is further monitored by the use of a dissolved oxygen probe which will measure the $O_2$ concentration in the reactor broth. In particular embodiments, the measurements gathered by the oxygen probe are used to control the inlet $O_2$ or air feed rate.

In particular embodiments, at least a portion of non-utilised gas and/or gas produced by the microorganism(s) exits the reactor through a gas outlet. This exit gas typically comprises unconsumed $CH_4$ and $O_2$, along with $CO_2$ produced by the microorganism. In particular embodiments, at least a portion of the exit gas is recycled back to the bioreactor for further conversion. In such embodiments, the exit gas may first undergo any gas separation process known in the art to remove one or more undesirable components of the exit gas stream, such as $CO_2$. Alternatively, at least a portion of the exit gas may be utilised as a fuel.

Extraction

In various embodiments, the lipid products are contained within the cell or in the cellular membrane. In these cases, the lipid products needs to be extracted from the bacterial biomass. Therefore, following the microbial conversion process in the reactor, the biomass is fed to an extraction zone.

The extraction zone may comprise multiple extraction units for different stages of the extraction process. As a first stage, the biomass may be provided to a cell disruption unit at a solids concentration amenable to pumping biomass (less than 40% solids and preferably between 1 and 10% solids) for pretreatment prior to lipid extraction. The pretreatment step may consist of either a chemical or physical treatment of the cell biomass, preferably either high-pressure homogenization, high temperature incubation (between about 50° C. and about 200° C., preferably between about 75° C. and about 90° C.) or acid or alkaline pretreatment (preferred concentrations of between about 1 and about 10% $H_2SO_4$ or NaOH, preferably between about 2 and about 4% $H_2SO_4$ or NaOH) or any combination of the above.

In further embodiments of the present invention, the disrupted cells may first undergo a dewatering step to remove some of the water contained in the fermentation broth before being directed to a solvent extraction process. Dewatering may comprise, for example but is not limited to, centrifugation, filtration, evaporation, or combinations thereof. Dewatering may result in a biomass portion containing disrupted cells with a water content less than the water content of the starting fermentation broth. In some embodiments of the present invention, the water content of a dewatered biomass containing disrupted cells and lipids may range from about 10 wt % water to about 60 wt % water.

The disrupted cells may then undergo a solvent extraction process at a ratio between about 100:1 and about 1:100 of wet biomass:solvent, or at a ratio of between about 10:1 to about 1:10, or a ratio of about 5:1 to about 1:5 or a ratio of about 2:1 to about 1:2. A preferred solvent for use at this stage is a solvent with a polarity compatible with the polarity of the lipid fraction and with a sufficiently low boiling point to render solvent removal easier, preferred solvents are short chain alcohol solvents for a highly polar lipid fraction in methanotrophic biomass, e.g. butanol or pentanol or short chain alkane solvents, for microbial non-polar lipids, e.g. hexane or heptane or a combination of polar and non-polar solvent. Other examples of solvents which can be used in the process of the invention are selected from the group consisting of methanol, ethanol, 1-propanol, n-butanol, isobutanol, isoamyl alcohol, 2-methyl-1-butanol, phenethyl alcohol, 1-pentanol, 1-hexanol, 1-heptanol, 1-octanol, 1-nonanol, 1-decanol, tryptophol, isopropanol, 2-butanol, 2-pentanol, 2-hexanol, cyclohexanol, tert-butyl alcohol, tert-amyl alcohol, 2-methyl-2-pentanol, 2-methylhexan-2-ol, 2-methylheptan-2-ol, 3-methyl-3-pentanol, 3-methylactan-3-ol, cyclopentane, cyclohexane, benzene, toluene, diethyl ether, dichloromethane, tetrahydrofuran, ethyl acetate, acetone, dimethylformamide, acetonitrile, dimethyl sulfoxide, and mixtures thereof. In particular embodiments, the product from the extraction process is further separated into a light phase, primarily comprising extracted lipids and solvent, and a heavy phase, primarily comprising water, spent biomass, and lipid/solvent carryover. In some embodiments of the present invention, separation of the light phase and heavy phase may be accomplished by gravimetric methods including but not limited to centrifugation and phase separators. In particular embodiments, a disk stack centrifuge is employed at the separation stage.

In some embodiments of the present invention, the solvent extraction step may be completed at a temperature ranging from about 0° C. to about 100° C. In some embodiments of the present invention, the solvent extraction step may be completed at a temperature ranging from about 20° C. to about 50° C. In still further embodiments of the present invention, the solvent extraction step may be completed at a temperature of about 0° C., about 10° C., about 20° C., about 30° C., about 40° C., about 50° C., about 60° C., about 70° C., about 80° C., about 90° C., or about 100° C.

In some embodiments of the present invention, the solvent extraction step may be carried out at a pressure ranging from about 35 kPa (5 psia) to about 13790 kPa (2000 psia) or from about 690 kPa (100 psia) to about 6,900 kPa (1000 psia) or from about 6,900 kPa (1000 psia) to about 13,790 kPa (2,000 psia) or from 97 kPa (14 psia) to about 172 kPa (25 psia).

In some embodiments of the present invention, the solvent extraction step may be completed in a time period ranging from about 1 minute to about 24 hours. In some further embodiments of the present invention, the solvent extraction step may be completed in a time period ranging from about 1 minute to about 60 minutes. In some further embodiments of the present invention, the solvent extraction step may be completed in a time period of about 1 minute, about 10 minutes, about 20 minutes, about 30 minutes, about 40 minutes, about 50 minutes, or about 60 minutes. In some further embodiments of the present invention, the solvent extraction step may be completed in a time period ranging from about 1 hour to about 24 hours. In some further embodiments of the present invention, the solvent extraction step may be completed in a time period of about 1 hour, about 2 hours, about 3 hours, about 4 hours, about 5 hours, about 6 hours, about 7 hours, about 8 hours, about 9 hours, about 10 hours, about 11 hours, about 12 hours, about 13 hours, about 14 hours, about 15 hours, about 16 hours, about 17 hours, about 18 hours, about 19 hours, about 20 hours, about 21 hours, about 22 hours, about 23 hours, or about 24 hours.

Following separation, the solvent may be stripped from the lipid product using distillation, and recycled to the extraction zone leaving a substantially pure lipids stream. In particular embodiments, the heavy phase containing the spent biomass is sent to an anaerobic digestion module. Alternatively the spent biomass can be used to produce single cell protein.

In particular embodiments, lipids extracted from the biomass may be further processed to provide fuels or other chemicals. For example, at least a fraction of the lipid product stream may be passed to a hydrotreating unit where the lipids can be converted to diesel fuel or diesel fuel components.

In another embodiment, the lipids can be converted to at least one chemical, fuel or fuel component selected from the group consisting of renewable diesel, biodiesel, hydrocarbons, fatty acid methyl esters (FAME) and fatty acid ethyl esters (FAEE) by means well known in the art. Various derivative chemicals, such as cleaning and personal care products, use components such as surfactants, fatty alcohols, and fatty acids, all of which lipids or lipid derivatives may be provided as a substitute. Further, various oleochemicals can be produced from lipids.

In particular embodiments, at least a portion of the heavy phase comprising spent biomass from the solvent extraction step is passed to an anaerobic digester unit. Within the anaerobic digester unit, the components of the heavy phase are converted to biogas by anaerobic digestion. The anaerobic digester unit may contain acidogenic bacteria, acetogenic bacteria and/or methanogenic bacteria. In a typical anaerobic digestion process, the acidogenic bacteria will first convert the organic polymers and amino acids into $CO_2$, $H_2$, $NH_3$ and organic acids. The acetogenic bacteria will then convert the resulting organic polymers into acetic acid, along with additional $CO_2$, $H_2$ and $NH_3$. Finally, the methanogenic bacteria convert the resulting acetic acid into $CH_4$ and $CO_2$.

In particular embodiments, at least a portion the biogas produced by the anaerobic digester is provided to the bioreactor, wherein the methane is utilised for further microbial conversion by the methanotrophic bacteria to one or more products. In alternative embodiments, at least a portion of the biogas produced by the anaerobic digester is provided to a gas turbine for power generation. Power generated by the gas turbine may then be used to power any step of the process of the invention as described herein.

EXAMPLES

Example 1

This example presents the general procedure for carrying out the experiments that follow. A liquid medium was prepared in a bioreactor by dissolving the following reagents in 1000 mL of deionized water.
0.2 g $MgSO_4 \times 7H_2O$
0.02 g $CaCl_2 \times 6H_2O$
1.00 g $KNO_3$
7.5 g NaCl The bioreactor was next autoclaved at 121° C. for 20 minutes and then cooled to 30° C. The bioreactor was fitted with a dissolved oxygen (DO) probe and a pH probe and all connected to a controller. Next air was sparged through the medium at a rate of 100 sccm/m for 12 hours. Trace elements, carbonate buffer and phosphate were added (2 mL, 25 mL and 20 mL respectively).

Trace Element Recipe:
1.0 g $Na_2$-EDTA
2.0 g $FeSO_4 \times 7H_2O$
0.8 g $ZnSO_4 \times 7H_2O$
0.03 g $MnCl_2 \times 4H_2O$
0.03 g $H_3BO_3$
0.2 g $COCl_2 \times 6H_2O$
0.6 g $CuCl_2 \times 2H_2O$
0.02 g $NiCl_2 \times 6H_2O$
0.05 g $Na_2MoO \times 2H_2O$
Fill to 1000 mL Phosphate Solution:
5.44 g $KH_2PO_4$
10.73 g $Na_2HPO_4$
Fill to 1000 mL Carbonate Solution:
1M $NaHCO_3$ 700 mL
1M $Na_2CO_3$ 300 mL Base control (3M NaOH) was connected and set to maintain the pH at 8.8.

The air flow was replaced with the particular gas being tested and samples were taken for gas chromatography every 45 minutes using auto-sampling during the run.

Finally, 50 mL of inoculum were added.

Example 2

Methanotrophic bacteria require iron for growth, methanol oxidation as well as respiration. It has been shown that methanotrophs can produce a Fe-chelating compound (Yoon et al., 2010; Matsen et al., 2013), and thus can grow at very low levels of the metal. We found that growth rate of 5GB1 strain depends on the availability of iron. Maximal growth occurs at high levels of iron 14.4 µM). *Methylomicrobium buryatense* strain 5GB1 cultures were grown in 50 ml of mineral medium, in 250 ml closed vials, supplemented with 50 ml of methane and different concentrations of $Fe^{++}$, added as $FeSO_4$.

TABLE 2

Growth parameters of the *Methylomicrobium buryatense* strain 5GB1 at different concentrations of $FeSO_4$

| Sample | Final OD | $Fe^{++}$ concentration (µM) | Td (h)* |
|---|---|---|---|
| 1 | 0.44 ± 0.03 | 0 | 6.3 |
| 2 | 1.10 ± 0.03 | 0.18 | 4.9 |
| 3 | 095 ± 0.03 | 0.36 | 4.7 |
| 4 | 1.10 ± 0.03 | 0.72 | 4.6 |
| 5 | 1.05 ± 0.03 | 1.8 | 4.3 |
| 6 | 1.12 ± 0.04 | 3.6 | 4.3 |
| 7 | 1.06 ± 0.03 | 7.2 | 4.3 |
| 8 | 1.04 ± 0.01 | 14.4 | 4 |

*$T_d$, doubling time.

Example 3

Cells were grown in batch culture using different growth conditions. Harvest 1 came from cells grown with unlimited $CH_4$ and $O_2$; Harvest 2 came from cells grown under limited $O_2$; and Harvest 3 from cells grown under limited $CH_4$. Whole cell transesterification was used to quantify fatty acids as fatty acid methyl esters (Total FAMEs) and to identify fatty acid profile of the cellular lipids. Cellular lipid content and fatty acid profiles varied with the growth conditions.

TABLE 3

Fatty acid content and profile of the lipid fraction in *M. buryatense* 5GB1

| Fatty Acid Profile | *M. buryatense* 5 GB1 whole biomass | | |
|---|---|---|---|
| (% total FAME) | Harvest 1 | Harvest 2 | Harvest 3 |
| C12:0\|Lauric Acid | 0.13 | 0.23 | 0.35 |
| C14:0\|Myristic Acid | 4.12 | 5.78 | 4.34 |
| C15:0 | 0.99 | 1.20 | 1.01 |
| C16:0\|Palmitic Acid | 20.02 | 18.24 | 14.91 |
| C16:1n9 (∂7) | 17.73 | 22.25 | 30.09 |
| C16:1n7 (∂9)\|Palmitoleic Acid | 33.56 | 29.98 | 19.60 |
| C16:1n6 (∂10) | 17.12 | 21.93 | 23.06 |
| C16:1n5 (∂11) | 3.91 | 3.99 | 5.70 |
| C18:0\|Stearic Acid | 2.09 | 0.65 | 0.49 |
| C18:1n7\|Vaccenic Acid | 0.29 | 0.32 | 0.43 |
| Total FAME (% DW) | 12.18 ± 0.11 | 7.31 ± 0.02 | 4.39 ± 0.03 |

Example 4

*Methylomicrobium buryatense* 5GB1 cultures were grown 250 ml of the mineral medium described above, in 1 L jars, supplemented with 750 ml of methane. Cells were collected by centrifugation, lyophilized and submitted for amino acid analysis to AminoAcids (https://www.aminoacids.com) for total amino acid profiling. The amino acid composition of the *Methylomicrobium*-based protein is shown in Table 4. The 5GB1 cell protein showed similar to fish-meal content of isoleucine and methionine, and had higher amounts of these amino acids when compared to BP protein. Furthermore, contrary to *Methylococcus capsulatus* biomass which comprise of 15% of nucleic acids, the biomass from *Methylomicrobium buryatense* 5GB1 has only 3-5% of nucleic acids

TABLE 4

Amino acid content of the *Methylomicrobium buryatense* strain 5GB1 cell protein

| Amino acid | mg/g CDW | g/100 g cell protein | BP protein[1] | Fish meal[1] |
|---|---|---|---|---|
| L-Aspartic acid | 53.73 ± 2.48 | 10.43 | 9.8 | 9.9 |
| L-Threonine* | 26.24 ± 1.47 | 5.09 | 5.7 | 4.6 |
| L-Serine | 20.05 ± 1.39 | 3.89 | 3.8 | 4.7 |
| L-Glutamic Acid | 70.45 ± 2.9 | 13.68 | 12.1 | 14.0 |
| L-Proline | 18.96 ± 1.22 | 3.68 | 3.9 | 4.4 |
| L-Glycine | 25.28 ± 1.42 | 4.91 | 6.6 | 6.4 |
| L-Alanine | 31.72 ± 1.84 | 6.16 | 8.0 | 6.2 |
| L-Cysteine | 3.105 ± 0.325 | 0.60 | 0.9 | 1.0 |
| L-Valine | 33.805 ± 1.815 | 6.56 | 6.8 | 5.6 |
| L-Methionine* | 15.77 ± 1.22 | 3.06 | 2.8 | 3.1 |
| L-Isoleucine* | 28.93 ± 1.58 | 5.62 | 3.8 | 4.8 |
| L-Leucine* | 45.12 ± 2.59 | 8.76 | 8.8 | 8.0 |
| L-Tyrosine* | 22.885 ± 1.295 | 4.44 | 3.9 | 3.5 |
| L-Phenylalanine* | 28.915 ± 1.625 | 5.61 | 4.8 | 4.1 |
| L-Tryptophan* | 14.7 ± 0.9 | 2.85 | 1.9 | 1.1 |
| L-Lysine* | 32.04 ± 1.91 | 6.22 | 6.4 | 8.1 |
| L-Histidine* | 12.095 ± 0.675 | 2.35 | 2.4 | 2.5 |
| L-Arginine* | 31.515 ± 1.815 | 6.12 | 7.5 | 6.6 |

*Essential amino acids; BP, BioProtein (based on *Methylococcus capsulatus* cell protein);
[1]data from http://www.vkm.no/dav/a0782dea9c.pdf

Example 5

This example describes some of the fermentation parameters generated during fed-batch and continuous culturing. In the fed batch runs, an initial medium and reactor setup as shown in Example 1 was run until the growth reached the stationary stage and gas uptake declined. The gas at the reactor inlet and outlet were measured on an hourly basis in order to determine the gas uptake, and the culture optical density was measured frequently as well to determine growth conditions.

For the methanol fed-batch run a similar procedure to Example 1 is used in order to carry out the experiment with methanol instead of methane as the carbon source. In addition to standard NMS2 medium, and additional 0.5% v/v of methanol is added prior to inoculation. Instead of a premixed gas blend, air is sparged through the medium at 100 sccm. The pH control, and gas chromatograph sampling do not change.

The specific $CH_4$ and $O_2$ uptake rates peaked at the highest growth rate and are summarized in the Table 5 below.

TABLE 5

Fame % of dry weight, specific $O_2$ uptake, and specific $CH_4$ uptake for methanol fed-batch, methane fed-batch, $O_2$ limited, and $CH_4$ limited runs

| | Methanol Fed-Batch | Methane Fed-Batch | $O_2$ Limited | $CH_4$ Limited |
|---|---|---|---|---|
| FAME as % dry weight | 6 | 8 | 11 | 12 |
| $O_2$ uptake (mmol hr$^{-1}$ g CDW$^{-1}$) | 9.4 | 23.8 | 15.4 | 7.1 |
| $CH_4$ Uptake (mmol hr$^{-1}$ g CDW$^{-1}$) | N/A | 16.4 | 6.9 | 8.1 |
| Inlet Gas Composition | Air | 10% CH4 5% O2 | 20% CH4 5% O2 | 2.5% CH4 20.3% O2 |

In a similar experiment, a fed batch culture was switched to continuous feed of medium, with the media components separated out into different solutions. This system was allowed to reach a steady state. Media component flow rates into the reactor were varied until one was found to be limiting. The specific $NO_3$ and $PO_4$ requirements for biomass were determined based on the steady state biomass concentration supported by the limiting nutrient flow.

TABLE 6

Ranges and typical values for key process parameters of specific $CH_4$ uptake, specific $O_2$ uptake, specific $NO_3$ uptake, specific $PO_4$ uptake, and specific Cu uptake.

| | Highest observed value | Lowest Observed value | Typical value |
|---|---|---|---|
| Specific $CH_4$ uptake (mmol hr$^{-1}$ g CDW$^{-1}$) | 17.6 | 6.9 | 8.8 |
| Specific $O_2$ uptake (mmol hr$^{-1}$ g CDW$^{-1}$) | 23.8 | 6.9 | 12.6 |
| Specific $NO_3$ Uptake required (mmol $NO_3$ g CDW$^{-1}$) | — | — | 5.7 |
| Specific $PO_4$ Uptake required (mmol $PO_4$ g CDW$^{-1}$) | 2 | 1.4 | 1.5 |
| Specific Cu Uptake required (µmol Cu g CDW–1) | 2.2 | 1.0 | |

Example 6

It is well known that copper plays a key role in the physiology and activity of aerobic methanotrophic bacteria. The growth of strains, possessing only particulate methane monooxygenase strongly depends on availability of the metal. Cultures with soluble MMO can grow without copper supplementation, however display reduced growth rate. Strain 5GB1 was able to switch to sMMO upon copper limitation and grew over a wide range of copper (0-20 µM). The growth rate of the strain without copper was 0.115 h$^{-1}$ (vs 0.24 h$^{-1}$ at optimal copper levels). The optimal copper concentrations were found to be 12 µM (added as $CuSO_4$). No growth of the strain was observed at copper concentrations above 24 µM. The amount of lipids accumulated was higher in cultures grown with copper as shown in the table below.

TABLE 7

Impact of Cu concentration on FAME % of CDW

| | Cu Concentration (µmol/L) | FAME as % CDW |
|---|---|---|
| Typical Cu concentration | 27.6 | 11.1 |
| | 13.8 | 12.6 |
| | 6.9 | 10.1 |
| | 3.5 | — |
| | 1.7 | 4.59 |
| | 0.9 | 5.86 |
| | 0.4 | 5.44 |

Example 7

This example describes a high cell density culture of our microorganism in a batch cultivation in a 0.5 L bioreactor. A culture medium used in this culture was modified as 8× nitrogen source, 2× phosphate solution, and 4× trace element solution in a liquid medium as set forth in Example 1. The ratio of $CH_4$ and $O_2$ in a blended gas was 1:0.8. Culture pH in the bioreactor was controlled and maintained at pH 8.8. The maximum cell density of 22 g/L was achieved in this 48 hr cultivation and is listed below.

| Time | DCW, g/L | Pr-DCW, g/L/h | FAME, % | FAME, mg/L | Pr-FAME, mg/L/h | C14:0 | C15:0 | C16:0 | C16:1 |
|---|---|---|---|---|---|---|---|---|---|
| 19 h | 3.36 | 0.18 | 8.32 | 559.35 | 29.44 | 3.44 | 0.83 | 15.73 | 78.39 |
| 24 h | 13.32 | 0.56 | 6.85 | 911.92 | 38.00 | 3.46 | 0.97 | 16.06 | 77.78 |
| 44 h | 22.44 | 0.51 | 4.35 | 975.69 | 22.17 | 4.32 | 1.46 | 15.13 | 76.56 |
| 48 h | 21.88 | 0.46 | 4.24 | 927.57 | 19.32 | 4.41 | 1.41 | 14.85 | 77.12 |

Example 8

This example presents a batch culture carried out in a 5 L bioreactor. The same culture medium, blended gas, and culture pH applied in Example 7 were used in this culture. A DCW of 10 g/L was obtained from this 72 hr culture, which was just half of the maximum DCW achieved in Example 7. This may be due to lower agitation rate constrained by this bioreactor. However, the FAME content was about 10% through this entire cultivation.

pressurized extraction on dried biomass using the following parameters; 75 mg dry biomass, extracted at 50° C. under 1500 psi, for three consecutive extractions. The solvent with extracted lipids was evaporated to dryness under a stream of nitrogen at 40° C. Chloroform:methanol consistently extracted 100% lipids, with butanol extracting 70% lipids. Fatty acid profile remained consistent, representative fatty acids were present in butanol extracted lipids and are shown below.

| Time | DCW, g/L | Pr-DCW, g/L/h | FAME, % | FAME, mg/L | Pr-FAME, mg/L/h | C14:0 | C15:0 | C16:0 | C16:1 |
|---|---|---|---|---|---|---|---|---|---|
| 24 h | 1.65 | 0.07 | 10.23 | 337.72 | 14.07 | 5.95 | 1.24 | 18.16 | 72.99 |
| 48 h | 9.87 | 0.21 | 10.02 | 988.60 | 20.60 | 3.85 | 0.99 | 18.57 | 75.22 |
| 72 h | 9.97 | 0.14 | 10.05 | 1002.05 | 13.92 | 7.49 | 1.30 | 18.05 | 71.47 |

Example 8

Solvent Compatibility with Lipid Types

The selective partitioning of polar and non-polar intact lipids in polar and non-polar solvents was demonstrated on pure components. Butanol was chosen as representative low-boiling short-chain alcohol solvent, forming a lighter phase with aqueous cell suspension, and compared to hexane as traditional lipid extraction solvent for triglyceride-based lipids. Using phosphatidylcholine as a representative polar lipid and pure canola oil as a representative for non-polar triglyceride lipids, comparison of extraction efficiency after dissolution of lipids in water and subsequent extraction with either hexane or butanol (at 1:1 ratio) showed 2.7% extraction of polar lipids in hexane, with significant emulsion formation inhibiting phase separation necessary for extraction, while 70% recovery in butanol was observed, with between 61-72% recovery of neutral lipids with both solvent types being obtained. Butanol separations were clean and effective for polar lipid extraction.

|  | % Recovery |
|---|---|
| Phosphatidylcholine (hexane extracted) | 2.7 |
| Phosphatidylcholine (butanol extracted) | 68.1 |
| Triglyceride (hexane extracted) | 61.2 |
| Triglyceride (butanol extracted) | 72.49 |

Demonstration of completeness of extraction of lipids on dry biomass, measured as fuel-relevant fatty acids, showed that 1-butanol was as good as more toxic polar solvent system chloroform:methanol (2:1) used for general analytical extractions and generally accepted to be complete. An accelerated solvent extractor (ASE, Dionex) was used for

|  | Chloroform:methanol | 1-butanol |
|---|---|---|
| C12:0\|Lauric Acid | 0.25 | 0.26 |
| C14:0\|Myristic Acid | 4.42 | 4.48 |
| C15:0 | 1.04 | 1.03 |
| C16:0\|Palmitic Acid | 15.37 | 14.75 |
| C16:1n9 (ə7) | 30.53 | 31.72 |
| C16:1n7 (ə9)\|Palmitoleic Acid | 18.39 | 17.49 |
| C16:1n6 (ə10) | 23.28 | 23.26 |
| C16:1n5 (ə11) | 5.78 | 6.15 |
| C18:0\|Stearic Acid | 0.57 | 0.51 |
| C18:1n7\|Vaccenic Acid | 0.38 | 0.35 |
| Total FAME (% DW) | 4.62 | 3.08 |
| Lipid purity (fatty acids from extracted Lipids) | 44.23 | 56.19 |
| Extraction yield (% completeness) | 105.2 | 70.2 |

Example 9

Demonstration of Increased Extraction Efficiency with Heat Treatment of Cell Suspension Incubation of between 1-10% cell suspension was heated for 15 min at 85° C., followed by 1 hr extraction at room temperature, with application to the biomass yielding between 4 and 28% fatty acid extractability when hexane was used, while 70% completeness of extraction with butanol. Heat treatment was found to be an effective way to rupture cells allowing for extraction and separation of polar and non-polar lipids. Potential mechanisms in which heat can help with cell rupture induction include denaturing of the proteins and destruction of the proteoglycan layer of the cells, thereby making the lipids more accessible to solvent extraction.

|  | Heat - hexane | Hexane - Heat | Heat - butanol |
|---|---|---|---|
| C12:0\|Lauric Acid | 1.31 | 0.13 | 0.21 |
| C14:0\|Myristic Acid | 2.94 | 4.85 | 5.33 |

-continued

|  | Heat - hexane | Hexane - Heat | Heat - butanol |
|---|---|---|---|
| C15:0 | 0.47 | 1.09 | 1.2 |
| C16:0\|Palmitic Acid | 26.27 | 16.71 | 18.47 |
| C16:1n9 (∂7) | 26.19 | 20.13 | 0 |
| C16:1n7 (∂9)\|Palmitoleic Acid | 17.41 | 28.24 | 37.93 |
| C16:1n6 (∂10) | 16.83 | 23.45 | 28.66 |
| C16:1n5 (∂11) | 4.57 | 4.28 | 7.11 |
| C18:0\|Stearic Acid | 3.46 | 0.6 | 0.51 |
| C18:1n7\|Vaccenic Acid | 0 | 0.34 | 0.43 |
| Lipid purity (fatty acids from extracted Lipids) | 9.75 ± 7.01 | 102.96 | 44.35 ± 2.55 |
| Extraction yield (% completeness) | 3.6 | 28.7 | 68.8 |

Embodiments of the invention are described by way of example. However, it should be appreciated that particular steps or stages necessary in one embodiment may not be necessary in another. Conversely, steps or stages included in the description of a particular embodiment can be optionally advantageously utilised in embodiments where they are not specifically mentioned.

While the invention is broadly described with reference to any type of stream that may be moved through or around the system(s) by any known transfer means, in certain embodiments, the substrate and/or exhaust streams are gaseous. Those skilled in the art will appreciate that particular stages may be coupled by suitable conduit means or the like, configurable to receive or pass streams throughout a system. A pump or compressor may be provided to facilitate delivery of the streams to particular stages. Furthermore, a compressor can be used to increase the pressure of gas provided to one or more stages, for example the bioreactor. As discussed hereinabove, the pressure of gases within a bioreactor can affect the efficiency of the fermentation reaction performed therein. Thus, the pressure can be adjusted to improve the efficiency of the fermentation. Suitable pressures for common reactions are known in the art.

In addition, the systems or processes of the invention may optionally include means for regulating and/or controlling other parameters to improve overall efficiency of the process. One or more processors may be incorporated into the system to regulate and/or control particular parameters of the process. For example particular embodiments may include determining means to monitor the composition of substrate and/or exhaust stream(s). In addition, particular embodiments may include a means for controlling the delivery of substrate stream(s) to particular stages or elements within a particular system if the determining means determines the stream has a composition suitable for a particular stage. For example, in instances where a gaseous substrate stream contains low levels of $O_2$ or high levels of $CH_4$ that may be detrimental to the microbial reaction, the substrate stream may be diverted away from the bioreactor. In particular embodiments of the invention, the system includes means for monitoring and controlling the destination of a substrate stream and/or the flow rate, such that a stream with a desired or suitable composition can be delivered to a particular stage.

In addition, it may be necessary to heat or cool particular system components or substrate stream(s) prior to or during one or more stages in the process. In such instances, known heating or cooling means may be used. For example, heat exchangers may be employed to heat or cool the substrate streams.

Furthermore, the system may include one or more pre/post treatment steps to improve the operation or efficiency of a particular stage. For example, a pre-treatment step may include means for removing particulate matter and/or long chain hydrocarbons or tars from a gaseous substrate stream. Other pre- or post-operations that may be conducted include separation of desired product(s) from particular stages, such as, for example, the bioreactor production stage.

The invention has been described herein with reference to certain preferred embodiments, in order to enable the reader to practice the invention without undue experimentation. Those skilled in the art will appreciate that the invention can be practiced in a large number of variations and modifications other than those specifically described. It is to be understood that the invention includes all such variations and modifications. Furthermore, titles, headings, or the like are provided to aid the reader's comprehension of this document, and should not be read as limiting the scope of the present invention.

More particularly, as will be appreciated by one of skill in the art, implementations of embodiments of the invention may include one or more additional elements. Only those elements necessary to understand the invention in its various aspects may have been shown in a particular example or in the description. However, the scope of the invention is not limited to the embodiments described and includes systems and/or methods including one or more additional steps and/or one or more substituted steps, and/or systems and/or methods omitting one or more steps.

The reference to any prior art in this specification is not, and should not be taken as, an acknowledgement or any form of suggestion that that prior art forms part of the common general knowledge in the field of endeavour in any country.

Throughout this specification and any claims which follow, unless the context requires otherwise, the words "comprise", "comprising" and the like, are to be construed in an inclusive sense as opposed to an exclusive sense, that is to say, in the sense of "including, but not limited to".

The invention claimed is:

1. A process for the production of lipids by microbial conversion of a gaseous substrate, comprising:
    (a) providing a gaseous substrate comprising $CH_4$ and $O_2$ at a ratio from about 5:1 to about 0.5:1 $O_2:CH_4$ to a bioreactor comprising a culture of *Methylomicrobium buryatense* microorganism in a liquid nutrient medium; and
    (b) microbially converting under fermentation conditions the gaseous substrate to lipids in the cellular membrane of the methanotrophic microorganism; and
    (c) extracting the lipids from the cellular membrane of the microorganism;
    wherein the fermentation conditions comprise:
        a partial pressure of the gaseous substrate from about atmospheric to about 3,000 kPag;
        a $Cu^{++}$ concentration in the liquid nutrient medium from about 7 to about 20 µM
        an $Fe^{++}$ concentration in the liquid nutrient medium from about 5 to about 15 µM;
        a $PO_4^{-3}$ concentration in the liquid nutrient medium sufficient to obtain a $PO_4^{-3}$ uptake from about 1.4 to about 2 mmol/gDCW; and
        a $NO^{-3}$ concentration in the liquid nutrient medium sufficient to obtain a $NO^{-3}$ uptake from about 5 to about 8 mmol/gDCW.

2. The process of claim 1, wherein the lipids are selected from the group consisting of fatty acids, glycolipids, sphingolipids, saccharolipids, polyketides, sterol lipids, hopanoids, phospholipids, prenol lipids, and mixtures thereof.

3. The process of claim 2, wherein the lipids are further converted into compounds selected from the group consisting of renewable diesel fuel, biodiesel fuel, diesel fuel, diesel components, fatty acid methyl esters and fatty acid ethyl esters.

4. The process of claim 1, wherein the gaseous substrate comprises $O_2$ and $CH_4$ at a ratio from about 1.3:1 to about 0.9:1 $O_2$:$CH_4$.

5. The process of claim 1, wherein at least a portion of the gaseous substrate exits the bioreactor unreacted through a gas outlet and is recycled back to the bioreactor for further conversion.

6. The process of claim 1, further comprising maintaining the pH of the liquid nutrient media in the range from about 6 to about 11.

7. The process of claim 1, further comprising maintaining the temperature of the liquid nutrient media in the range from about 5 to about 50° C.

8. The process of claim 1, wherein the methanotrophic microorganism also produces a product selected from the group consisting of proteins, and amino acids.

9. The process of claim 1, wherein the extracting step comprises a cell disruption step and a solvent extraction step.

10. The process of claim 9, wherein the cell disruption is achieved by heating the microorganism and the solvent used in the solvent extraction is butanol.

11. The process of claim 9, wherein the solvent extraction step produces a light phase comprising lipids and a heavy phase comprising spent biomass.

12. The process of claim 11, wherein at least of portion of the spent biomass is used to prepare single cell protein.

13. The process of claim 11, further comprising passing at least a portion of the heavy phase to an anaerobic digester where at least a portion of the heavy phase is converted to biogas.

14. The process of claim 13, wherein at least a portion of the produced biogas is provided to the bioreactor.

15. The process of claim 1 where the microorganism is *Methylomicrobium buryatense* strain 5GB1.

16. A process for the production of lipids by microbial conversion of a substrate comprising:
(a) providing a substrate comprising oxygen and at least one component selected from $CH_3OH$ or a mixture of $CH_3OH$ and $CH_4$ to a bioreactor comprising a liquid nutrient media and a culture of *Methylomicrobium buryatense* microorganism characterized in that the $CH_3OH$ concentration in the liquid nutrient media varies from about 0.5% (v/v) to about 5% (v/v);
(b) microbially converting under fermentation conditions the substrate to produce lipids in the cellular membrane of the microorganism; and
(c) extracting the lipids from the cellular membrane of the microorganism;

wherein the fermentation conditions comprise:
a partial pressure of the gaseous substrate from about atmospheric to about 3,000 kPag;
a $Cu^{++}$ concentration in the liquid nutrient medium from about 7 to about 20 µM;
an $Fe^{++}$ concentration in the liquid nutrient medium from about 5 to about 15 µM;
a $PO_4^{-3}$ concentration in the liquid nutrient medium sufficient to obtain a $PO_4^{-3}$ uptake from about 1.4 to about 2 mmol/gDCW; and
a $NO^{-3}$ concentration in the liquid nutrient medium sufficient to obtain a $NO^{-3}$ uptake from about 5 to about 8 mmol/gDCW.

17. The process of claim 16, wherein the lipids are selected from the group consisting of fatty acids, glycolipids, sphingolipids, saccharolipids, polyketides, sterol lipids, hopanoids, phospholipids, prenol lipids, and mixtures thereof.

18. The process of claim 16, wherein when the substrate is $CH_3OH$ and $CH_4$ the $O_2$ and $CH_4$ are present at a ratio ranging from about 5:1 to about 0.5:1 $O_2$:$CH_4$.

19. The process of claim 18, further characterized in that the microorganism uptakes $CH_4$ and $O_2$ at a ratio from about 1:1 to about 2.5:1 $O_2$ to $CH_4$.

20. The process of claim 16, further comprising when the substrate is oxygen, $CH_3OH$, and $CH_4$, blending the $CH_4$ with the $CH_3OH$ prior to the substrate being provided to the bioreactor.

21. The process of claim 16, wherein the extracting step comprises a cell disruption step and a solvent extraction step.

22. The process of claim 21, wherein the solvent extraction step produces a light phase comprising lipids and a heavy phase comprising spent biomass.

23. The process of claim 22, wherein at least of portion of the spent biomass is used to prepare single cell protein.

24. The process of claim 22, further comprising passing at least a portion of the heavy phase to an anaerobic digester where at least a portion of the heavy phase is converted to biogas.

25. The process of claim 24, wherein at least a portion of the produced biogas is provided to the bioreactor.

26. The process of claim 21, wherein the cell disruption is achieved by heating the microorganism and the solvent used in the solvent extraction is butanol.

27. The process of claim 16, further comprising converting at least a portion of the extracted lipids to at least one compound selected from the group consisting of renewable diesel, biodiesel, diesel, diesel derivatives, fatty acid methyl esters and fatty acid ethyl esters.

28. The process of claim 16, wherein the methanotrophic microorganism also produces a product selected from the group consisting of proteins, and amino acids.

29. The process of claim 16 where the microorganism is *Methylomicrobium buryatense* strain 5GB1.

* * * * *